United States Patent [19]
Blayo et al.

[11] Patent Number: 5,739,909
[45] Date of Patent: Apr. 14, 1998

[54] MEASUREMENT AND CONTROL OF LINEWIDTHS IN PERIODIC STRUCTURES USING SPECTROSCOPIC ELLIPSOMETRY

[75] Inventors: Nadine Blayo, Pontivy; Arnaud Grevoz, Creteil, both of France; Tseng-Chung Lee, New York, N.Y.

[73] Assignee: Lucent Technologies Inc., Murray Hill, N.J.

[21] Appl. No.: 543,570

[22] Filed: Oct. 10, 1995

[51] Int. Cl.⁶ .............................. G01B 11/02; G01N 21/21
[52] U.S. Cl. ..................................... 356/369; 356/381
[58] Field of Search .............................. 356/364, 365, 356/366, 367, 369, 381, 382, 384

[56] References Cited

U.S. PATENT DOCUMENTS

| | | | |
|---|---|---|---|
| 4,763,183 | 8/1988 | Ng et al. | 357/23.7 |
| 5,114,233 | 5/1992 | Clark et al. | 356/354 |
| 5,539,766 | 7/1996 | Ishino et al. | 372/96 |

OTHER PUBLICATIONS

B. Drévillon, "Progress in Crystal Growth and Characterization of Materials", 1993, vol. 27, pp. 1–87, Pergamon Press.

R. H. Krukar, "Methodology for the Use of Diffracted Scatter Analysis to Measure Critical Dimensions of Periodic structures" Ph.D. Tesis University of New Mexico, 1993, CH. 3, pp. 10–18.

Primary Examiner—Richard A. Rosenberger

[57] ABSTRACT

A non destructive method of spectroscopic ellipsometry adapted to measure the width of features in periodic structures, particularly those features which are less than one micron wide. The method is also adapted to make comparisons between a known reference structure and a sample structure, and to control the fabrication of periodic structures in a plasma etching reactor. Peaks in functions DELTA and PSI versus wavelength are monitored and correlated against reference curves, permitting etching conditions to be modified. This technique avoids the need for use of scanning electron microscopy to measure the linewidth, which is a destructive method. It also posses an advantage over scatterometry which requires several detectors arrayed at different angles from an incident beam to measure the different diffracted orders.

18 Claims, 5 Drawing Sheets

MEASUREMENT AND CONTROL OF LINEWIDTHS IN PERIODIC STRUCTURES USING SPECTROSCOPIC ELLIPSOMETRY

BACKGROUND OF THE INVENTION

1. Field of the Invention

This invention relates to the measurement and control of features in a periodic structure, and in particular to the measurement and control of lines which are one micron or less in width by spectroscopic ellipsometry.

2. Description of Related Art

Advances in computing power and information sharing are the result of increased speed of semiconductor devices and increased bandwidth of communications links. The increased speed of the semiconductor devices such as processors and memories requires tighter design rules so that features are now being formed on these devices which are less than one micron in width. Similarly, the transmitters for optical fiber links, such as distributed feedback lasers, require the generation of periodic structures with sub-micron features.

Processing methods to generate sub-micron features typically employ plasma etching, with or without a bias on the workpiece which directs ions toward the surface being etched. Particular ions are selected to etch and remove a film to form a space while selectively leaving a patterned mask in place over the areas which are designated to be features. The processing conditions are selected to be anisotropic, meaning that the vertical etch rate is maximized while the lateral etch rate (which would undercut the mask) is minimized. By modifying the constituents of the plasma or the electrical bias applied to the workpiece, the sidewalls of the feature may be tapered, vertical, or undercut. With proper conditions, aspect ratios (height compared to the width of a feature) greater than ten have been achieved, but controlling the production of, or even measuring, sub-micron features is increasingly difficult.

Linewidths have been measured by cleaving a sample after processing and examining it in a scanning electron microscope. This is a destructive, time consuming, test which cannot rapidly provide feedback of processing information to improve that particular wafer or lot. Scatterometry has also been used to measure linewidths, but this process requires several detectors arranged at different angles from an incident beam to measure different diffracted orders.

For example, U.S. Pat. No. 5,114,233 given to Clark et al., teaches a method for inspecting etched workpieces wherein a beam of coherent light is directed at the workpiece and the intensity of scattered light is measured over several orders of diffraction. A spatial frequency is then computed for each intensity measurement. The scattered light is detected by a photodiode which is preferably mounted on a rotating arm whose axis is aligned to the target area of the workpiece. The angular range is about 90 degrees to 180 degrees in which several hundred intensity measurements are made and recorded. An envelope of intensity versus spatial frequency is next approximated to form a matrix from which principal components are determined. Correlations are made to etching characteristics of the workpiece, such as undercut profiles or tapered profiles. While this is a nondestructive test, it would be difficult to implement for in-situ processing in a vacuum chamber because of the range of diffracted angles that need to be scanned.

The art of ellipsometry is well known and has been used to measure the thickness of various films (R. M. A. Azzam and N. M. Bashara, "Ellipsometry and Polarized Light", North Holland, 1987). If ordinary white light is sent through a polarizer, it emerges as linearly polarized light in which its electric field vector is aligned with an axis of the polarizer. Linearly polarized light can be defined by two vectors, parallel and perpendicular to the plane of incidence. If the parallel vector is out of phase with the perpendicular vector, the result is elliptically polarized light. If both vectors are in phase, the result is circularly polarized light. Ellipsometry is based on the polarization transformation that occurs when a beam of polarized light is reflected from a medium. The transformation consists of two parts: a phase change and an amplitude change. These changes are different for incident radiation with its electric vector oscillating in the plane of incidence (p-component) compared to the electric vector oscillating perpendicular to the plane of incidence (s-component). Ellipsometry measures the results of these two changes which are conveniently represented by an angle DELTA ($\Delta$), which is the change in phase of the reflected beam from the incident beam; and an angle PSI ($\Psi$), which is defined as the arc tangent of the amplitude ratio of the incident and reflected beam. Since the reflected beam is fixed in position relative to the incident beam, ellipsometry is an attractive technique for in-situ control of processes which take place in a chamber. The angle of incidence and reflection are equal, but opposite in sign, to each other and may be chosen for convenience in directing the beam into the chamber.

For example, U.S. Pat. No. 5,131,752 given to Yu et al., teaches the use of ellipsometry to monitor the thickness of a film as it is deposited on a workpiece. The method is limited to planar surfaces.

Accordingly, there is an increased need in the art of measurement and in process control for a method to accurately measure the dimensions of periodic features, particularly those with dimensions in the range of less than one micron to a few microns. The method should be nondestructive and amenable to in-situ process control as the features are being etched in a chamber. Additionally, in-situ process control should also have the advantage to improve yield, contribute to uniformity across a wafer and across a lot, and thereby improve device reliability.

SUMMARY OF THE INVENTION

The present invention relates to the inspection and comparison of periodic features which range in width from a few microns to less than one micron. The invention also relates to a method of in-situ process control for the etching of periodic features. The method employs spectroscopic ellipsometry which plots the angles $\Delta$ and $\Psi$ as a function of wavelength ($\lambda$).

In one embodiment of the invention, an incident beam of elliptically polarized light is directed at a periodic structure which has a pitch comprising a feature and a space. A reflected beam coming from the periodic structure at an angle which is equal, but opposite in sign, to the angle the incident beam makes with the periodic structure is detected and its intensity and polarization are determined at a first wavelength. The change in phase between the incident beam and the reflected beam are used to calculate an ellipsometric parameter such as $\Delta$ or $\Psi$. The change in phase between the incident beam and the reflected beam is used to calculate an angle $\Delta$. The ratio of amplitudes of the incident beam and the reflected beam are used to calculate an angle $\Psi$. The values of $\Delta$ and $\Psi$ are compared to reference values of $\Delta$ and $\Psi$. If they are within a specified control range the sample is accepted as having feature linewidths in an acceptable range of linewidths.

In another embodiment of the invention, the process described above is repeated for at least one additional wavelength. The wavelengths selected are within a factor of ten (an order of magnitude) of the width of the feature in a periodic structure. The width of the feature is calculated from Δ and Ψ at the selected wavelengths. If the first wavelength is out of specification, then the second wavelength indicates whether the linewidth is wider or narrower than desired, based on whether its value increases towards a peak or decreases away from a peak. The process for the next wafer can then be adjusted accordingly. A preliminary scan may be taken at wavelengths which are equivalent to energies (E) ranging from 1.5 eV (electron volt) to 5.0 eV. The wavelength in nanometers is λ=1240/E, where the energy is in electron volts. The preliminary scan indicates where the amplitude of the reflected beam is highest and around which a more detailed scan may be taken to calculate the angles Δ and Ψ.

In yet another embodiment of the invention, peaks in the angles Δ and Ψ as a function of wavelength, as described above, are used to determine the linewidth of features which are being etched in a plasma chamber containing reactive ions. The peaks are compared to reference values and the concentration of ions such as chlorine or oxygen is varied to provide in-situ process control. Bias power to the workpiece may also be raised to promote faster etching and therefore obtain a straighter wall with more anisotropic etching.

These and other features and advantages of the invention will be better understood with consideration of the following detailed description of the preferred embodiments taken in conjunction with the accompanying drawings.

The drawings are not to scale.

DETAILED DESCRIPTION OF THE PREFERRED EMBODIMENTS

Figure 1:
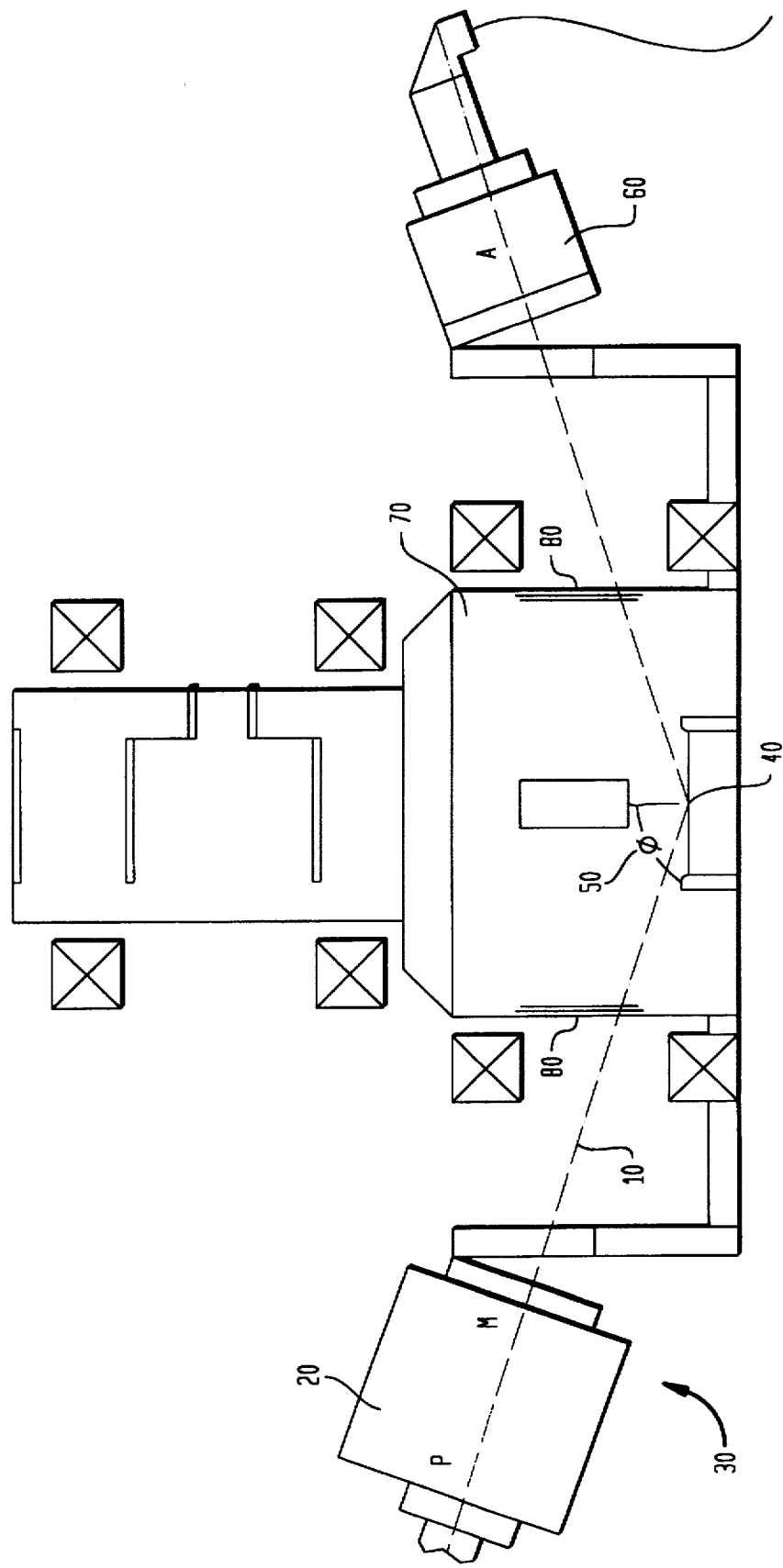
FIG. 1 is a schematic illustration of an ellipsometer as used in the present invention.

Referring now to FIG. 1, there is shown an ellipsometer which is arranged so that an incident beam is directed through a window at a workpiece within a reactor and a reflected beam from the workpiece is detected outside the reactor. The incident beam 10 is generated by excitation head 20 of ellipsometer 30. Optical fiber 25 transports white light from a source (not shown) to head 20. The incident beam 10 is directed to workpiece 40 through reactor window 80 so that the angle of incidence 50 measured from the normal to workpiece 40 is about 70 degrees. Other angles of incidence are contemplated as useful, depending on the workpiece, and angles of about zero degrees to about 90 degrees are contemplated. The reflected beam leaves the workpiece at an angle which is equal, but opposite in sign, to the angle of incidence, passes through window 80, then through an analyzer, and then to a monochromator through an optical fiber. The monochromator selects a particular wavelength of light which is transmitted to a detector which converts the optical signal to an electrical signal which enters a signal processor. Angles Δ and Ψ are determined from a numerical signal processing system, for example, as described in *Progress in Crystal Growth and Characterization of Materials*, 1993, Vol. 27, pp. 1–87, Pergamon Press.

The determination is made with coupled wave analysis to solve for scattered fields resulting from a plane wave which is obliquely incident upon a periodic structure. The model solves a system of state equations which are derived from the wave equation and a set of boundary equations. In the case of ellipsometry, the model was applied to the specularly reflected beam at a constant angle (having the same absolute value as the angle of the incident beam) to determine Δ and Ψ as a function of energy. The analysis was performed by dividing the volume around the periodic structure into three slabs which are parallel to the plane of the sample. The first slab is the region above the periodic structure which includes the incident and reflected beams. The second is the region of the periodic structure. This region is as thick as the material from which the feature is formed. The third slab is the substrate which supports the periodic structure. This slab could be a semiconductor, for example. The expressions for the electric field vector were written for each slab. For example, in the first slab the electric field is expressed as the sum of the incident field and the reflected field. Next, the propagation equation of the electric field was written for each slab to obtain a second-order differential system. Boundary conditions were applied which require the continuity of the electric field at each interface, and a linear system of equations were solved to get reflectance coefficients of the periodic structure from which the ellipsometric angles Δ and Ψ were determined. The details of the analysis can be found in "A Methodology for the Use of Diffracted Scatter Analysis to Measure the Critical Dimensions of Periodic Structures", R. H. Krukar, Ph.D. Thesis, University of New Mexico, 1993 (Chapter 3, pp. 10–18)

Chamber 70 is suitable for etching films from workpiece 40. As used here, the term "plasma etching" shall encompass plasma etching with or without a bias applied to the workpiece. Biasing the workpiece causes reactive ions to strike it with energy which increases the anisotropy of etching which is desirable for vertical sidewalls of features.

Figure 2:
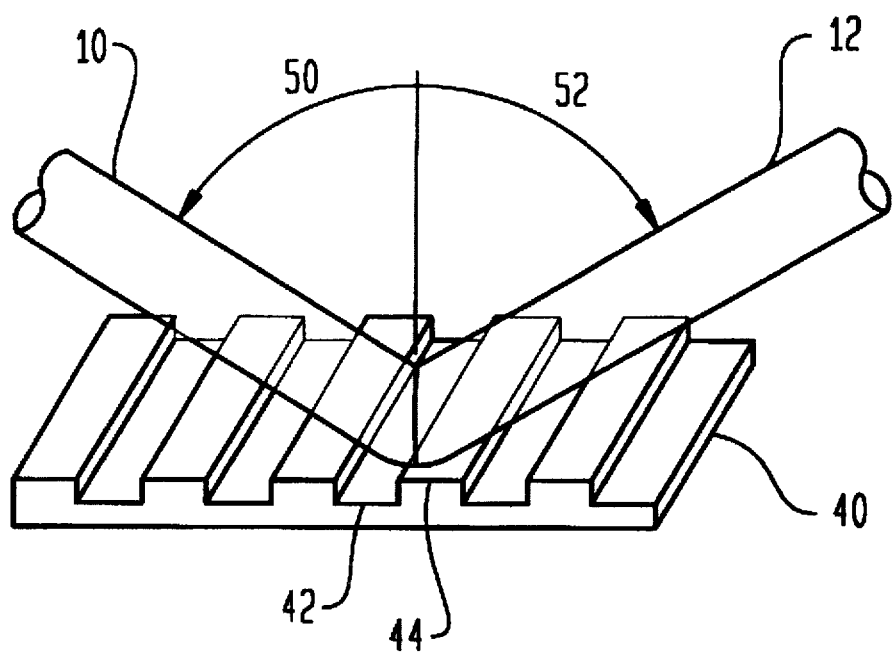
FIG. 2 shows a beam being reflected from a workpiece containing features in a periodic structure.

Referring now to FIG. 2, there is shown a workpiece 40 having a periodic structure of features 42 and spaces 44. The width of a feature added to the width of a space equals the pitch of the periodic structure. Incident beam 10 from the excitation head, previously described, and reflected beam 12 lie in a plane which is approximately perpendicular to the longitudinal axis of feature 42. In practice, an alignment of the features to plus or minus two degrees from the normal to the plane of incidence and reflection is easily achieved and this tolerance does not degrade the quality of the data. The diameter of beams 10 and 12 can be adjusted by an aperture to be between 2 and 10 millimeters. Preferably, the periodic structure fills the area of the incident beam, but applicants believe that filling a significant fraction of the incident beam will also provide meaningful data.

The features on a workpiece are typically parallel segments of lines and spaces where the lines may range from 10 microns to a few tenths of a micron in width. Periodic structures are used in the fabrication of electronic devices such as semiconductor microprocessors and memories, transmission devices such as distributed feedback lasers, and microwave devices. The substrates supporting the periodic structure may be an insulator, a semiconductor, or a compound semiconductor used in laser fabrication. The feature to be defined by etching is covered by a mask which is typically photoresist or an oxide, and the material of the line may be a metal, a refractory metal silicide, a nitride, or an oxide. These materials are in common use in semiconductor processing. For example, 0.3 micron wide polysilicon lines, 5000 angstroms thick, have been made and measured with a 2500 angstrom thick silicon dioxide mask.

Figure 3A:
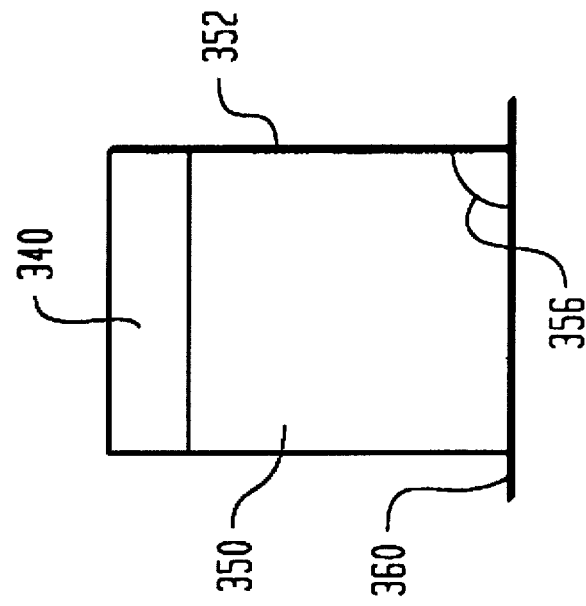
FIGS. 3A and 3B are cross-sectional views of various etching profiles.
Figure 3B:
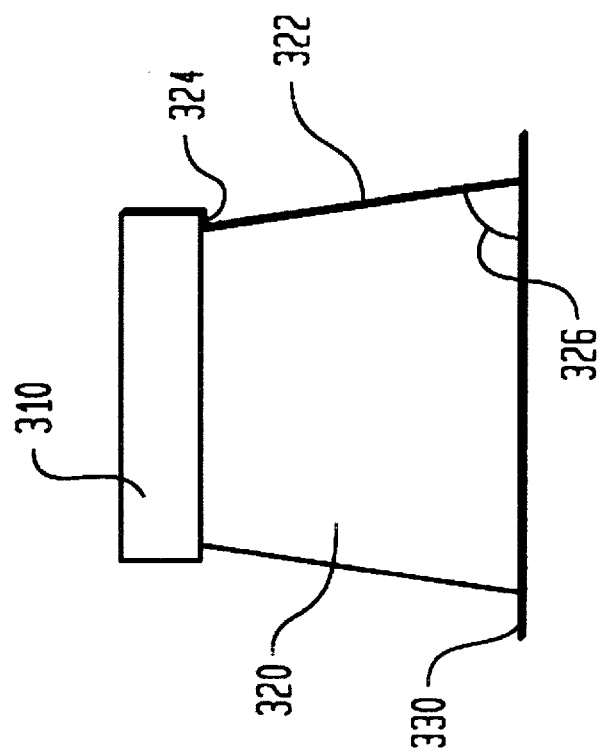

Referring now to FIG. 3A, there is shown a cross section of a feature 320 which may be comprised of any of the materials mentioned above which supports a mask 310. The feature resides on a substrate 330 which may be an insulator or a semiconductor. Sidewall 322 intercepts the substrate at an angle 326. As the etching process continues, a slight degree of undercutting may occur causing step 324 to form under the mask making the feature narrower where it has been exposed to a longer period of etching. Isotropic etching is typified by a larger step 324 and a smaller angle 326 than anisotropic etching. Semiconductor device fabrication usually seeks to achieve anisotropic etching with vertical sidewalls for fine lines which is depicted in FIG. 3B. Substrate 360 intercepts sidewall 352 of feature 350 at an angle 356 which is 90 degrees. Mask 340 is supported by the feature and the mask is not undercut in this case.

In one embodiment of the invention, workpiece 40 shown in FIG. 2 is aligned perpendicular to the plane of incident beam 10 and reflected beam 12. A misalignment of the features to plus or minus two degrees from the normal to the plane of incidence has been shown to be tolerable. The angle of incidence of incident beam 50 and the angle of reflected beam 52 measured from the normal to the workpiece are equal and may range from nearly zero degrees to nearly 90 degrees. In this example, the angles are plus and minus 70 degrees, respectively. Incident beam 10 is elliptically polarized and is directed at a periodic structure 40 which has a pitch comprising a feature and a space. Reflected beam 12 is detected and its intensity and polarization are determined at a first wavelength. The change in polarization between the incident beam and the reflected beam are used to calculate an angle Δ. The ratio of amplitudes of the incident beam and the reflected beam are used to calculate an angle Ψ. The sample is accepted if the values of the angles are within a specified range.

In another embodiment of the invention, the process described above is repeated for at least one additional wavelength. The wavelengths selected are within an order of magnitude (a factor of ten) the width of feature 42. The width of the feature is calculated from Δ and Ψ at the selected wavelengths. If the first wavelength is out of specification, then the second wavelength indicates whether the linewidth is wider or narrower than desired, based on whether its value increases towards a peak or decreases away from a peak. The process for the next wafer can then be adjusted accordingly. A preliminary scan may be taken at wavelengths which are equivalent to energies (E) ranging from 1.5 eV (electron volt) to 5.0 eV. The wavelength in nanometers is λ=1240/E, where the energy is in electron volts. The preliminary scan indicates where the amplitude of the reflected beam is highest and around which a more detailed scan may be taken to calculate the angles Δ and Ψ.

Figure 4:
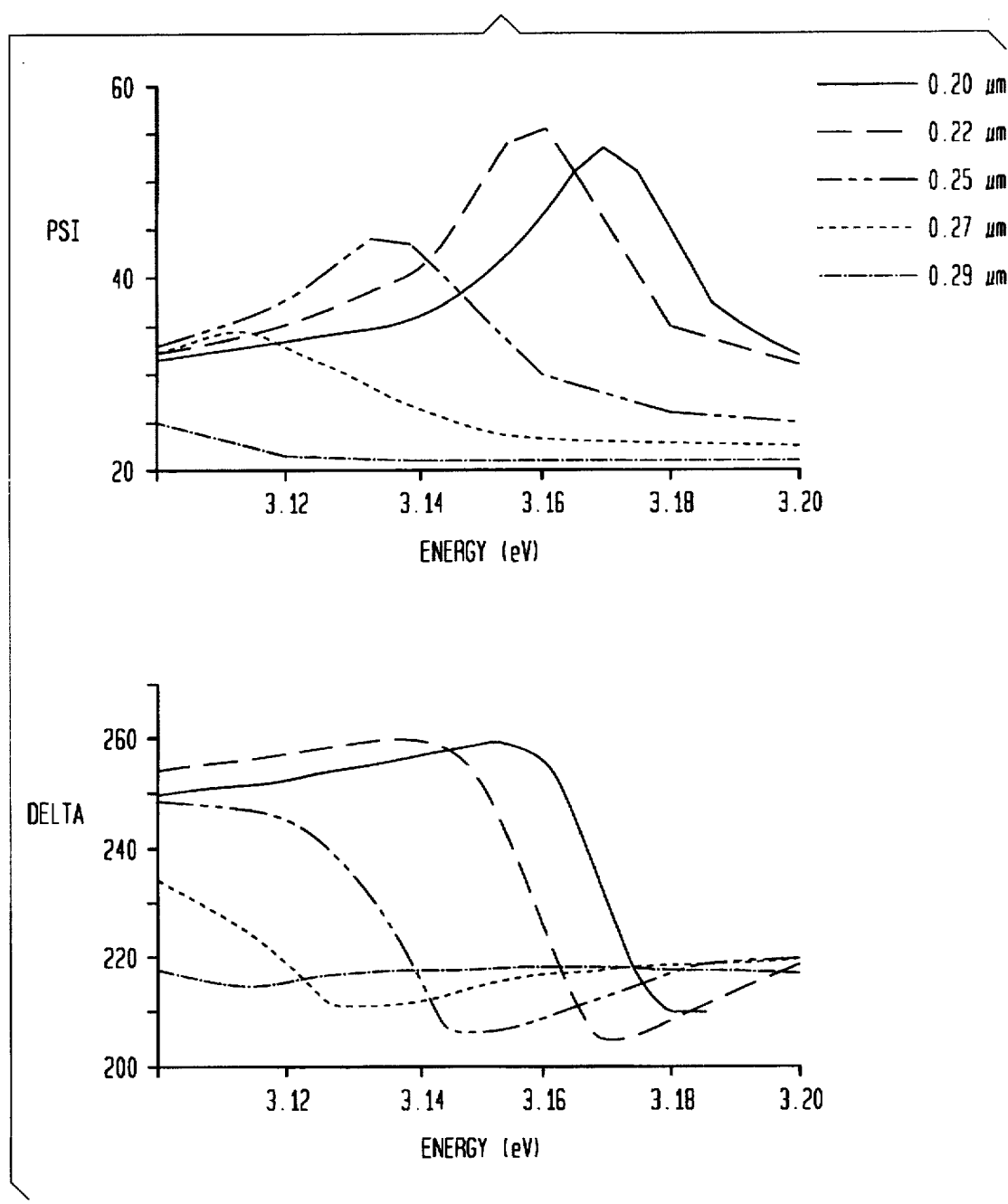
FIG. 4 shows calculated peak values in the functions Δ and Ψ as a function of energy for a coupled wave analysis.

Referring now to FIG. 4, there are shown theoretical curves of Δ and Ψ versus energy for polysilicon features of various widths in a periodic structure having a constant pitch of 0.6 microns supported by a silicon substrate. The peaks in the curves of Ψ progress toward lower energy as the width of the feature increases from 0.20 microns to 0.29 microns. The curves also become flatter with increasing linewidth. The theoretical curves for Δ follow a similar pattern.

Figure 5:
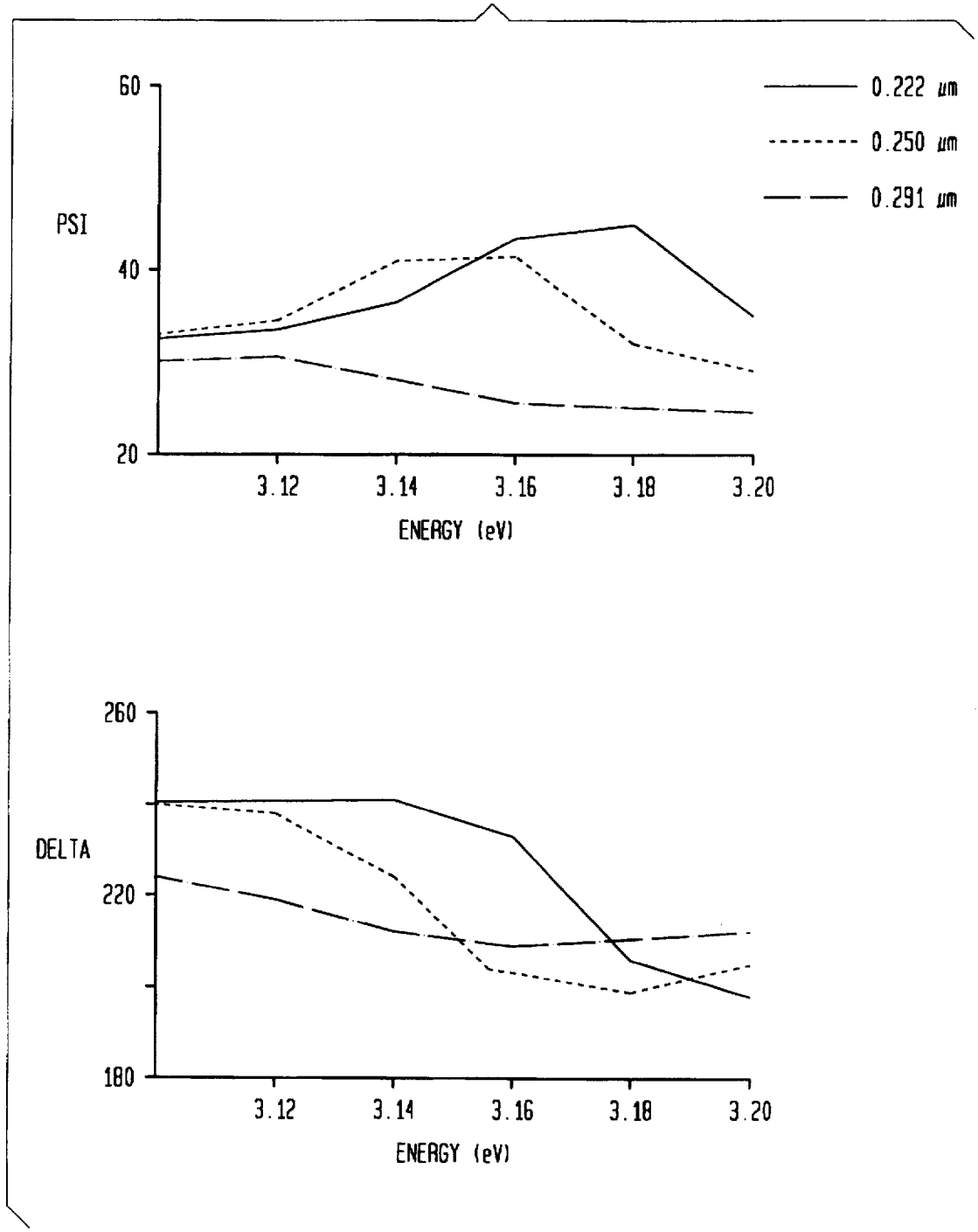
FIG. 5 shows experimental results of Δ and Ψ as a function of energy which relate to the linewidth of a feature in a periodic structure.

Referring now to FIG. 5 there are shown traces of experimentally determined angles Δ and Ψ versus energy. The peaks shift toward lower energy values as the width of the feature increases; just as predicted by the coupled wave analysis. In this case the width of the features was supposed to be 0.3 microns, but it varied due to processing conditions. The pitch was constant at 0.6 microns. A full spectroscopic scan was taken from 1.5 eV (826 nm) to 5.0 eV (248 nm) to determine the variation of Δ and Ψ versus energy (wavelength). A peak was observed around 3.1 eV, so measurement were taken in increments of 0.02 eV from 3.0 eV to 3.2 eV to determine the peak more clearly, although smaller increments could have been taken. The position of the peak, as well as the shape of the curve, changed with linewidth. There was good agreement between the experimental data and the calculations from the coupled wave analysis model (FIG. 4), which shows that spectroscopic ellipsometry is able to discriminate between different linewidths to a precision of plus or minus five nanometers. The linewidths of the samples were later confirmed by a topdown scanning electron microscope showing that the actual linewidths were 0.220, 0.250, and 0.291 microns for various samples. For these polysilicon films, an "amorphous model", which considered the material to be 5% crystalline and 95% amorphous, provided a better fit to experimental data than a "crystalline model" in which the proportions were reversed. It was also determined that a sidewall with a taper of five degrees from the normal to the substrate had no effect upon the linewidth determination.

In yet another embodiment of the invention, peaks in the angles Δ and Ψ as a function of wavelength as shown in FIG. 5, are used to determine the linewidth of features which are being etched in a plasma chamber containing reactive ions (See FIG. 1). The peaks are compared to reference values, and when there is a deviation, steps may be taken to change processing conditions to return to the reference value. For example, the concentration of reactants such as chlorine or oxygen may be varied to control the slope of the sidewall. Bias power to the workpiece may also be altered. Raising the power adds greater momentum to the impinging ions, promoting faster etching in the vertical direction, and therefore obtaining a straighter wall which is characteristic of anisotropic etching.

The advantages of spectroscopic ellipsometry to measure and characterize periodic structures are that it is quick and non-destructive; particularly in measuring sub-micron features which commonly require cross-sectioning and scanning electron microscopy. The method is useful to measure the dimensions of periodic features, to compare a reference periodic feature to another one, or to control fabrication of a periodic feature in-situ in a highly reactive environment such as a plasma etching reactor. Insitu process control should also improve yield, contribute to uniformity across a lot, and improve device reliability.

Changes and modifications in the specifically described embodiments can be carried out without departing from the scope of the invention.

We claim:

1. A method of inspecting a periodic structure having a pitch comprising a feature and a space, comprising:

directing an incident beam of elliptically polarized light at the periodic structure for obtaining a reflected beam;

detecting the reflected beam for determining its intensity and polarization at a first wavelength;

comparing the change in phase between the incident beam and the reflected beam for calculating an angle Δ;

finding the ratio of the amplitude of the incident beam to the reflected beam for calculating an angle $\Psi$; and determining if the values of $\Delta$ and $\Psi$ are within a specified control range for accepting the periodic structure:

wherein the values $\Delta$ and $\Psi$ are used to determine that the periodic structure is accepted as having feature linewidths in an acceptable range of linewidths.

2. The method of claim 1 wherein the first wavelength is of the same order of magnitude as the pitch of the periodic structure.

3. The method of claim 1 wherein the first wavelength is between 248 m and 827 nm.

4. A method of inspecting a periodic structure having a pitch comprising a feature and a space, comprising:

directing an incident beam of elliptically polarized light at the periodic structure for obtaining a reflected beam;

detecting the reflected beam for determining its intensity and polarization at a first wavelength;

comparing the change in phase between the incident beam and the reflected beam for calculating an angle $\Delta$;

finding the ratio of the amplitude of the incident beam to the reflected beam for calculating an angle $\Psi$;

detecting the reflected beam for at least one additional wavelength;

comparing the change in phase between the incident beam and the reflected beam of the at least one additional wavelength for calculating an angle $\Delta$;

finding the ratio of the amplitude of the incident beam to the reflected beam of the at least one additional wavelength for calculating an angle $\Psi$; and determining the width of the features in the periodic structure.

5. The method of claim 4 wherein the first wavelength and the at least one additional wavelength are of the same order of magnitude as the pitch of the periodic structure.

6. The method of claim 4 wherein the first wavelength and the at least one additional wavelength are between 248 nm and 827 nm.

7. A method of in-situ process control of a plasma etching process for the generation of a periodic structure having a pitch comprising a feature and a space, comprising:

directing an incident beam of elliptically polarized light at the periodic structure for obtaining a reflected beam;

detecting the reflected beam for determining its intensity and polarization at a plurality of wavelengths;

comparing the change in phase between the incident beam and the reflected beam for calculating an angle $\Delta$ at each wavelength;

finding the ratio of the amplitude of the incident beam to the reflected beam for calculating an angle $\Psi$ at each wavelength;

determining the peak of $\Delta$ and $\Psi$ versus wavelength;

comparing the peaks of $\Delta$ and $\Psi$ to desired reference peak values of $\Delta$ and $\Psi$; and changing process parameters to reduce changes between peak values determined during processing to the desired reference peak values of $\Delta$ and $\Psi$.

8. The method of claim 7 wherein the plurality of wavelengths are of the same order of magnitude as the pitch of each periodic structure.

9. The method of claim 7 wherein the range of wavelengths is between 248 nm and 827 nm.

10. The method of claim 7 wherein changing process parameters comprises altering the plasma chemistry in a plasma etching process to increase the taper of a sidewall of a feature.

11. The method of claim 7 wherein changing process parameters comprises altering the plasma chemistry in a plasma etching process to provide more undercut to a sidewall of a feature.

12. The method of claim 7 wherein changing process parameters comprises increasing the RF bias power to the workpiece in a plasma etching process to control the degree of anisotropic etching.

13. The method of claim 7 wherein changing process parameters comprises altering the plasma source power to the workpiece in a plasma etching process to control the degree of anisotropic etching.

14. The method of claim 7 wherein the periodic structure is a grating.

15. The method of claim 7 wherein the feature in the periodic structure is an electrical conductor.

16. The method of claim 7 wherein the feature in the periodic structure is an electrical insulator.

17. The method of claim 7 wherein the features in the periodic structure comprise elements of a distributed feedback laser.

18. The method of claim 7 wherein the features in the periodic structure comprise elements of a wave guide component.

* * * * *